US00PP08545P

United States Patent [19]

Toyama

[11] Patent Number: Plant 8,545

[45] Date of Patent: Jan. 18, 1994

[54] SWEET CHERRY TREE PC 7146-23

[75] Inventor: Thomas K. Toyama, Eugene, Oreg.

[73] Assignee: Washington State University Research Foundation, Pullman, Wash.

[21] Appl. No.: 996,700

[22] Filed: Dec. 24, 1992

[51] Int. Cl.[5] ..... A01H 5/00

[52] U.S. Cl. ..... Plt./37

[58] Field of Search ..... Plt. 37

*Primary Examiner*—James R. Feyrer

*Attorney, Agent, or Firm*—Chernoff, Vilhauer et al.

[57] ABSTRACT

A new and distinct variety of sweet cherry tree which bears medium to large, dark red, mahogany colored, firm fruits is described. Its broadly cordate shaped, attractive fruits ripen 14 days ahead of the commercially grown Bing variety which it is compared to herein.

3 Drawing Sheets

BACKGROUND AND SUMMARY OF THE INVENTION

The present invention relates to a new and distinct variety of sweet cherry tree which bears medium to large, firm, attractive fruits of excellent quality and flavor.

This new variety was developed at the Washington State University's Irrigated Agriculture Research and Extension Center (I.A.R.E.C.) at Prosser, Wash. from a cross made in 1971. It was selected from among 141 seedlings of the cross Stella×Beaulieu (both unpatented) and tested and evaluated as selection PC 7146-23. Second test trees were planted on the Roza Unit of the center in the spring of 1979 and came into production in 1982.

The new sweet cherry variety ripens 14 days before Bing (unpatented commercial variety) and resembles Bing in shape and appearance (FIG. 1). The trees have been consistently productive bearing fruits comparable in size and as firm as Bing. The fruit is Bing-shaped, glossy and attractive when mature (FIG. 2).

Fruit stems are medium length and slightly shorter than those of Bing (FIG. 1). Fruit shape is broadly cordate, similar to Bing (FIGS. 1 and 2) and flesh is medium to dark red.

The new variety is not self-fruitful but is compatible with the Bing and Rainier (both unpatented) varieties which are grown commercially in the Pacific Northwest and other western states. It blooms 1-2 days before Bing and forms flower buds in exceptionally large numbers.

Fruit buds of PC 7146-23 have better winter hardiness than Bing as demonstrated by the recent winter freeze of December 1990 which severely reduced the Bing crop. Bud kill at I.A.R.E.C. after that freeze was determined to be 14% for PC 7146-23 and 71% for Bing. The tree is vigorous and spreading in shape (FIG. 5) and has proven to be a very precocious and fruitful bearer of early season high quality cherries. It may require special handling in order to prevent overbearing which can result in smaller sized fruits. Good fruit size can be maintained by heavier pruning.

Soluble solids is equal to or slightly less than Bing but fruit kept in cold storage at 33°-34° F. for four weeks stored better than Bing.

Susceptibility to rain cracking is rated moderate. The very firm, low acid fruits possess high dessert quality equal to the Bing variety.

The seeds are semi-freestone and small.

Several second and third generation trees observed closely have shown no tendency toward the "cherry crinkle-leaf" genetic disorder which is common in the Bing variety as well as several other varieties of sweet cherry.

Interest in this new clone is for a firm, early, high quality shipping variety for the early season fresh market.

Trees of the subject variety are vigorous and compatible with common rootstocks used under sweet cherry trees.

Asexual reproduction of this new and distinct variety show that its unique and desirable characteristics come true to form and are established and transmitted through succeeding propagations by grafting at our test facilities near Prosser, Wash.

BRIEF DESCRIPTION OF THE DRAWINGS

In the accompanying photographs (FIGS. 1, 2, 3, 4, and 5) trees, vegetative growth, and fruit are shown in color as nearly true as is reasonably possible to make in color photographs of this nature.

DETAILED DESCRIPTION OF THE INVENTION

Figure 1:
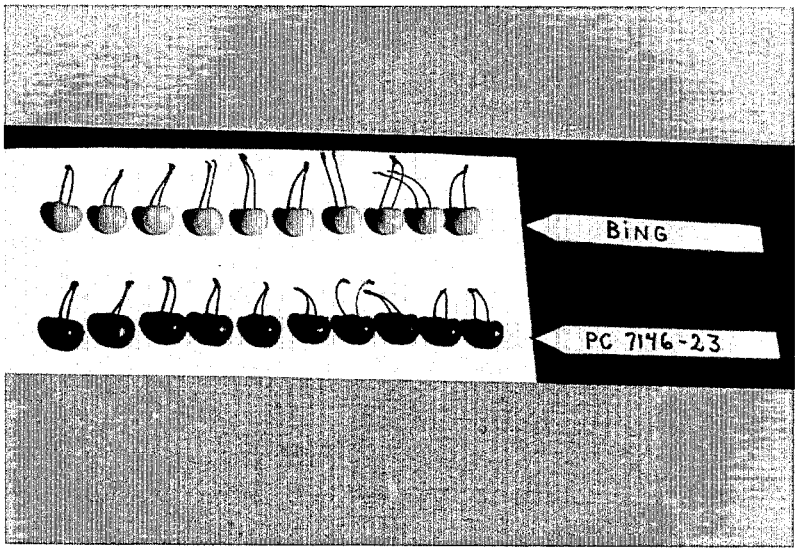
FIG. 1 shows and compares PC 7146-23 and Bing fruits which were picked from adjacent trees on May 22, 1992 near Wapato, Wash.
Figure 2:
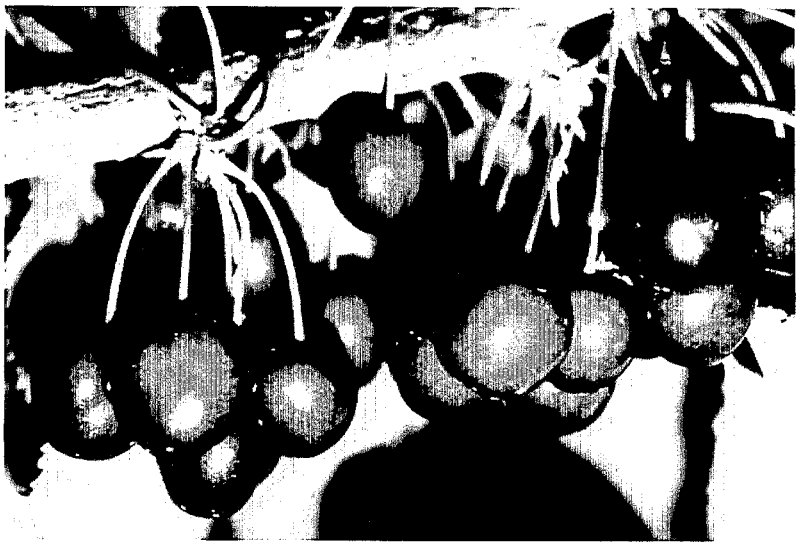
FIG. 2 shows a branch with clusters of fruit attached of the subject variety.
Figure 3:
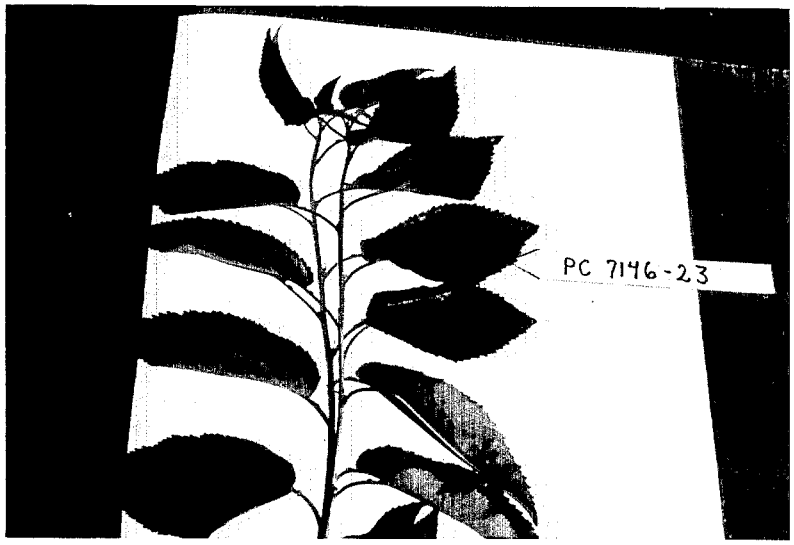
FIG. 3 shows leaves and fruiting spurs without fruit attached of the subject variety.
Figure 4:
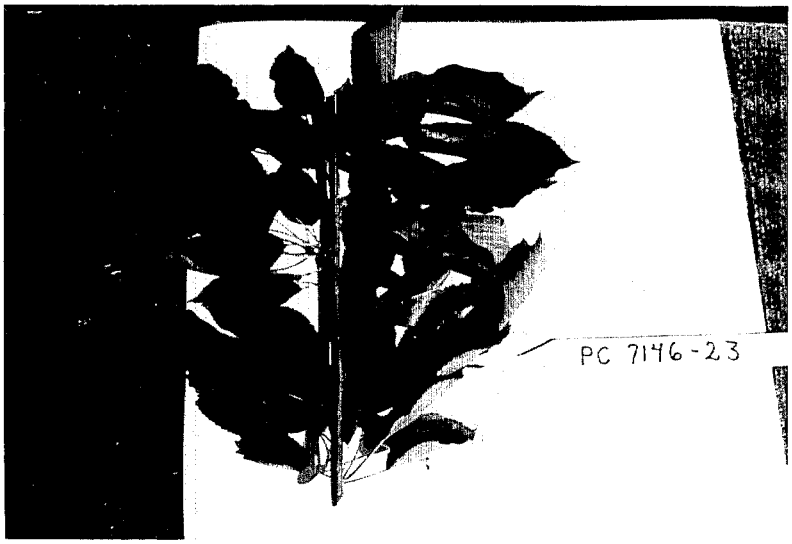
FIG. 4 shows current-season's vegetative growth and leaves of the subject variety.
Figure 5:
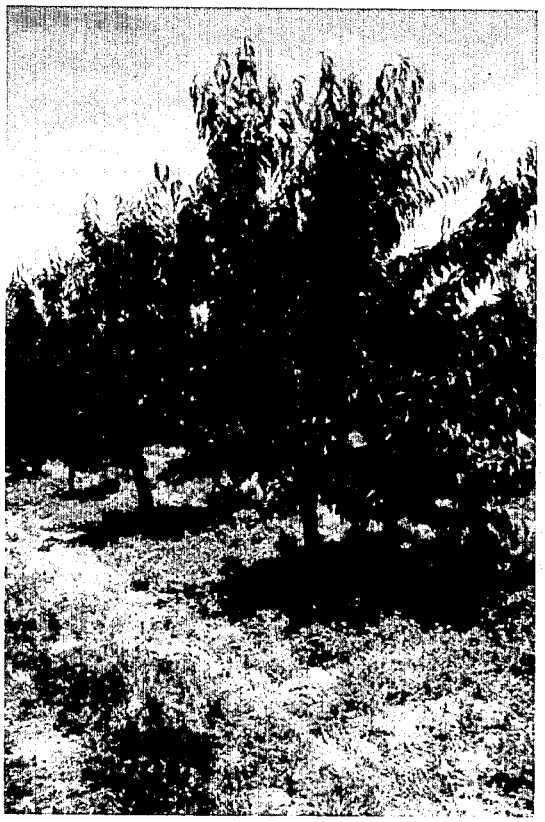
FIG. 5 shows several young fourth-leaf trees established in a trial test block near Wapato, Wash. of the subject variety.

Following is a detailed description of the new variety of cherry tree with color terminology in accordance with the Munsell Color Cascade Chart except where general color terms of ordinary dictionary significance are used.

Tree:

*Size.*—Large.
*Vigor.*—Vigorous.
*Branching habit.*—Upright-spreading.
*Density.*—Average for sweet cherry.
*Form.*—Round-headed when mature.
*Hardiness.*—Hardy in area where tested (Lower Yakima Valley of Washington).
*Production.*—Very productive.
*Bearing.*—Consistent, regular.
*Trunk.*—Size: Stocky. Bark texture: Typical for sweet cherry. Bark color: Grey-brown (26-13). Lenticels: Numerous, medium 3.2–5.5 mm in diameter, brown.
*Branch.*—Size: Stocky. Texture: Average, typical for sweet cherry. Color: First year wood, greenish-brown (32-10); second year wood, grey-brown (24-13). Lenticels: Numerous, small, 1.5–2.0 mm in diameter, brown.

Leaves: (Measurements are from mature leaves attached at midpoint of actively growing upright shoots of current-seasons growth.
*Size.*—Large, 16–18 cm long, 7.5–8.5 cm wide.
*Form.*—Lanceolate with acuminate tip.
*Color.*—Upper surface, glossy-green (20-13), lower surface, light brown (17-10).
*Midvein.*—Medium, pink (40-9), 1.5 mm in diameter.
*Petiole.*—Long 4.5–5.0 cm, thick 2.3 mm, light green (19-9) with pink tinge along petiole groove.
*Texture.*—Smooth.
*Margin.*—Crenate to finely serrate.
*Glands.*—Variable in number but mostly two, compressed, positioned both alternate and irregular, medium, oval to reniform shape, shiny with reddish center when immature, darker red (38–14) when mature, glabrous, positioned on rim of petiole groove 4–8 mm from base of leaf petiole.
*Stipules.*—Medium, usually two in number, 1.4–2.0 cm in length, light green (18-8).

Flower buds:
*Hardiness.*—Hardy.
*Size.*—Medium
*Length.*—Medium.
*Form.*—Medium length, plump, conic free.

Flowers: Self sterile.
*First bloom.*—April 5 at Prosser test site (5-year average), early as compared with other varieties.
*Full bloom.*—April 12 at Prosser test site.
*Size.*—Large, 25–30 mm in diameter when fully open.
*Color.*—White.
*Bloom count.*—Abundant, 5–9 per spur cluster.
*Petals.*—Average, 20 mm in length and 15 mm in width, obovate, cupped slightly inward, white.
*Nectaries.*—Grey-green when mature (22-8).
*Anthers.*—Large, yellow (27-4).
*Pollen.*—Abundant, yellow (27-6).
*Pedicel.*—Medium length 13 to 15 mm, light green (23-7).

Fruit:
*Maturity.*—Eating ripe June 6 at Prosser test site (1986–1991 six-year average).
*Date of first picking.*—June 6 at Prosser.
*Date of last picking.*—June 14 at Prosser.
*Size.*—Medium large 8.5 grams, diameter transversely across suture 2.5–2.7 cm, diameter apically 2.1–2.3 cm.
*Form.*—Uniform, symmetrical, broadly cordate, blunt apex end.
*Suture.*—Very shallow, very slight darker mahogany colored line extends from base to apex.
*Stem cavity.*—Broad, rounded shoulders, shallow.
*Base.*—Rounded.
*Apex.*—Slightly rounded to blunt, pistil point apical and distinctive.
*Stem.*—Medium thick, variable 3.2–3.8 cm in length, light green (21-8).
Skin.—Thickness: Medium. Texture: Medium. Tenacity: Tenacious to flesh. Tendency to crack: Susceptible to cracking caused by rain, mostly circular cracks at stem end and small splits at tip end of fruit, none in dry season, similar to Bing. Down: Wanting. Color: Mahogany red (41-16).
*Flesh.*—Color: Red (40-12). Surface of pit cavity: Dark red (39-14). Texture: Very firm, very crisp. Fibers: Few, cream color, fine. Ripens: Evenly. Flavor: Sweet, low acid, rich. Juice: Red (40-12). Aroma: Slight. Eating quality: Good.
*Stone.*—Type: Semi-free. Size: Small, 1.0–1.2 cm long and 1.0 cm wide. Form: Oval to globose with small protruding wing along basal shoulder of ventral suture. Base: Rounded. Helium: Small, oval to slightly oblong. Apex: Rounded. Sides: Equal. Surface: Smooth. Ventral edge: Narrow suture subtended by two low ridges converging basally and apically. Dorsal edge: Narrow, smooth, narrow ridge from base to apex. Color: Tannish-white when dry. Tendency to split: None.

Use: Early season shipping, fresh market.
Keeping quality: Good to excellent.
Resistance to insects and disease: No particular susceptibility noted. No cherry crinkle leaf noted.
Shipping quality: Firm, excellent, at least as good as Bing.
Variance in botanical details: The cherry tree and its fruit herein described will vary due to climatic, soil, and growing conditions under which the variety may be grown. The present description being of the variety as grown in the Lower Yakima Valley of Washington. Comparisons to the Bing cherry are referenced to Bing cherry trees growing in the same area under similar circumstances.

What is claimed is:

1. A new and distinct variety of cherry tree obtained as a seedling of the cross Stella × Beaulieu (both unpatented) is characterized by its early maturing firm fruits that ripen 14 days earlier than the fruits of the Bing variety.

* * * * *

UNITED STATES PATENT AND TRADEMARK OFFICE

CERTIFICATE OF CORRECTION

PATENT NO. : PP 8,545

DATED : January 18, 1994

INVENTOR(S) : Thomas K. Toyama

It is certified that error appears in the above-indentified patent and that said Letters Patent is hereby corrected as shown below:

Column 3, Line 25: delete "light brown"
insert --light green--

Signed and Sealed this

Eleventh Day of October, 1994

*Attest:*

*Attesting Officer*

Bruce Lehman

BRUCE LEHMAN

*Commissioner of Patents and Trademarks*